United States Patent [19]

Enomoto et al.

[11] Patent Number: 4,526,894

[45] Date of Patent: Jul. 2, 1985

[54] PHARMACEUTICALLY ACTIVE 4-HYDROXY-3-BENZOYL-2-QUINOLONE DERIVATIVES

[75] Inventors: Hiroshi Enomoto, Nagoakakyo; Tadatoshi Nomura, Uji; Yoshiaki Aoyagi, Otsu; Shoichi Chokai, Kameoka; Tatsuhiko Kono, Suita; Masao Murase, Kusatsu; Kichiro Inoue, Fushimi; Masahiro Adachi, Hirakata, all of Japan

[73] Assignee: Nippon Shinyaku Co. Ltd., Japan

[21] Appl. No.: 506,503

[22] Filed: Jun. 21, 1983

[30] Foreign Application Priority Data

Jun. 21, 1982 [JP] Japan .................. 57-107366

[51] Int. Cl.³ .................... A61K 31/47; C07D 215/22
[52] U.S. Cl. .................... 514/312; 546/155; 560/21
[58] Field of Search .......... 546/155; 424/258

[56] References Cited

U.S. PATENT DOCUMENTS 3,753,991  8/1973  Sturm et al. ............ 546/155
4,086,349  4/1978  Morinaka et al. ........ 546/155 X
4,476,132 10/1984  Göschke et al. ......... 424/258

FOREIGN PATENT DOCUMENTS 2556405  6/1976  Fed. Rep. of Germany .
2806879  8/1979  Fed. Rep. of Germany .

OTHER PUBLICATIONS

Tomita et al., Chemical Abstracts, vol. 46, 5044b–5045f (1952).
Vul'fson et al., Chemical Abstracts, vol. 54, 24733i (1960).
Ukita et al., Chemical Abstracts, vol. 58, 8238d (1963).
Moszew et al., Chemical Abstracts, vol. 72, 31585k (1970).
Venturella et al., Chemical Abstracts, vol. 83, 178,773f (1975).
Coppola et al., Chemical Abstracts, vol. 92, 146,570g (1980).
Morinaka et al., Eur. J. Med. Chem. 1981, 16(3), pp. 251–256 (cf. CA. 95,13710c).

*Primary Examiner*—Diana G. Rivers
*Attorney, Agent, or Firm*—Jacobs & Jacobs

[57] ABSTRACT

4-Hydroxy-2-quinolone derivatives are useful for their anti-inflammatory, anti-allergenic, antitussive and expectorant activity. Pharmaceutical compositions containing said compounds and pharmaceutically acceptable salts thereof and methods of treating humans and animals are described herein.

15 Claims, No Drawings

PHARMACEUTICALLY ACTIVE 4-HYDROXY-3-BENZOYL-2-QUINOLONE DERIVATIVES

The present invention is concerned with 4-hydroxy-2-quinoline derivatives, processes for their production, pharmaceutical compositions wherein said compounds or pharmaceutically acceptable salts thereof are the active agent and to methods of effecting anti-inflammatory, anti-allergenic, antitussive and expectorant action in humans and animals utilizing said compounds.

Sodium chromoglicate reported by Cox et al in *Advances in Drug Research*, vol. 5, p.115 (1970) is known to be effective for allergic asthma. However, that compound is believed to inhibit emission of chemical mediators from most cells but has the disadvantage that it does not show any effect on oral administration and the duration of its action is rather short.

It has recently been discovered that SRS-A (slow reacting substance of anaphylasis) which is one of the chemical mediators which plays a main role at the onset of asthma offers an area which, if one could develop new and specific pharmaceutical antagonizing agents against the action of SRS-A, a significant advance in the art would result.

More specifically, the present invention is concerned with compounds of the formula (I):

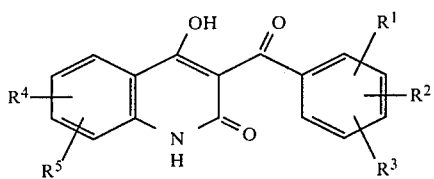

or a pharmaceutically acceptable salt thereof, wherein $R^1$, $R^2$, $R^3$, $R^4$ and $R^5$ are each hydrogen, alkyl of 1 to 8 carbon atoms, alkoxy of 1 to 5 carbon atoms, halo, nitro, cyano, halo lower alkyl of 1 to 3 carbon atoms or $COOR^6$ wherein $R^6$ is hydrogen or alkyl of 1 to 3 carbon atoms, provided that all of $R^1$, $R^2$, $R^3$, $R^4$ and $R^5$ are not simultaneously hydrogen. These compounds are useful for their anti-inflammatory activity, anti-allergenic action, as antitussives and as expectorants. They have been found to exhibit strong SRS-A-antagonizing action and to inhibit the synthesis of SRS-A.

These compounds and their pharmaceutically acceptable salts are particularly useful because of their ability to provide the above therapeutic properties on oral administration, while conventional known agents are not effective on oral administration. In addition, the therapeutic action is of a longer duration than compounds presently known in the art.

Examples of alkyl groups which are useful according to the present invention are methyl, ethyl, propyl, isopropyl, butyl, isobutyl, tert butyl, pentyl, hexyl, heptyl, octyl and the like. Examples of alkoxy groups useful according to the present invention are methoxy, ethoxy, propoxy, isopropoxy, butoxy, tert butoxy and the like. Suitable halo atoms include fluoro, chloro, bromo and iodo. Examples of suitable halo lower alkyl groups according to the present invention include trifluoromethyl.

Compounds of the formula (I) may also exist in tautomeric forms:

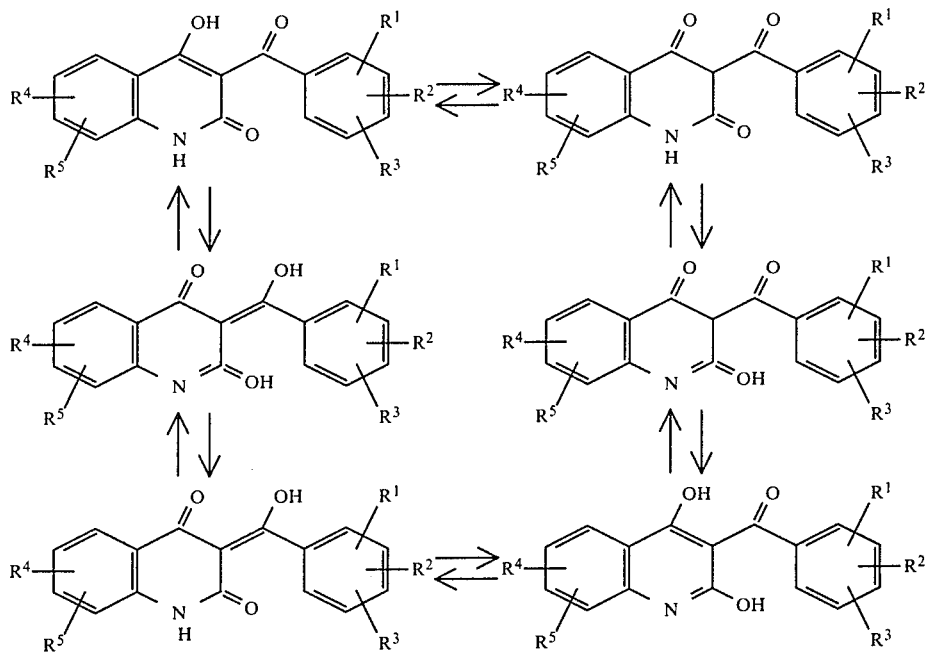

The compounds of the present invention and tautomers thereof may be prepared by a variety of methods. According to one process, compounds of the formula (II):

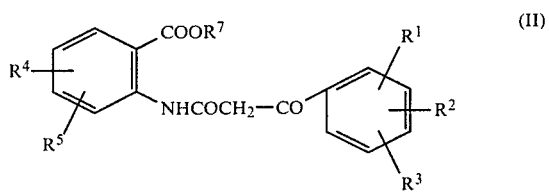

wherein $R^1$, $R^2$, $R^3$, $R^4$ and $R^5$ are as above defined; and $R^7$ is lower alkyl, for example methyl, ethyl, propyl or butyl, are subjected to ring closure in the presence of a basic substance. Suitably, the reaction is conducted at an elevated temperature, for example, 50° C. to 130° C. for from one to ten hours. The reactants are preferably dissolved in a suitable solvent such as methanol, ethanol, benzene, toluene, xylene, tetrahydrofuran, dimethyl formamide or the like, and the reaction carried out in the presence of a base such as, for example, metal sodium, sodium hydride, sodium alkoxide, triphenyl methyl sodium, potassium hydroxide, calcium hydroxide or the like.

Compounds of the formula (II) may be obtained by reacting a compound of the formula (III):

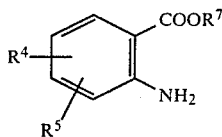

wherein $R^4$, $R^5$ and $R^7$ are as above defined with a compound of the formula (IV):

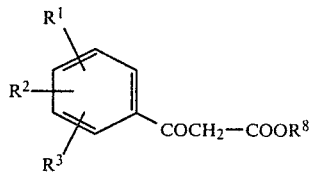

wherein $R^1$, $R^2$ and $R^3$ are as above defined and $R^8$ is hydrogen or lower alkyl, for example, methyl, ethyl, propyl or butyl, or a suitable cation, at a temperature of from 130° C. to 250° C. for from one to twenty-four hours when $R^8$ is lower alkyl. When $R^8$ is hydrogen or a suitable cation, the conducted at reaction is from 0° C. to 50° C. for from three to twenty-four hours, in a suitable solvent such as tetrahydrofuran, dimethyl formamide or the like, in the presence of a condensation agent.

The compounds of the present invention of the formula (I) may also be prepared by subjecting a compound of the formula (V):

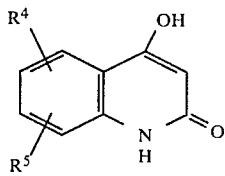

wherein $R^4$ and $R^5$ are as above defined, and a compound of the formula (VI):

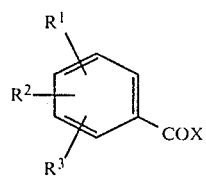

wherein $R^1$, $R^2$ and $R^3$ are as above defined and X is halo, to a Friedel-Crafts reaction at a temperature of from room temperature to 150° C. for from two to twenty hours in the presence of a Lewis acid, such as, for example, aluminum chloride, antimony pentachloride, ferrous chloride, ferric chloride, stannic chloride, zinc chloride, titanium tetrachloride, and the like, in a suitable solvent such as, for example, nitrobenzene, carbon disulfide, methylene chloride, carbon tetrachloride or 1,2-dichloroethane or the like.

Compounds of the formula (I) may also be prepared by producing a compound of the formula (VII):

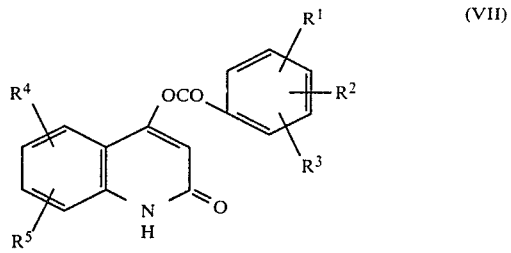

wherein $R^1$, $R^2$, $R^3$, $R^4$ and $R^5$ are as above defined, and subjecting said compound to a Fries rearrangement.

Compounds of the formula (V) may be prepared by heating an N-acetylanthranilate of the formula (VIII):

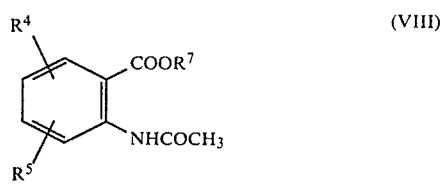

wherein $R^4$, $R^5$ and $R^7$ are as above defined at a temperature of from 50° to 130° C. for one to twelve hours in the presence of a base such as metal sodium, sodium hydride, triphenylmethyl sodium, potassium hydroxide, calcium hydroxide or the like in a suitable solvent such as, for example, methanol, ethanol, benzene, toluene, xylene, tetrahydrofuran or dimethylformamide.

Alternatively, a compound of the formula (V) may also be prepared by heating malonic anilide monoanilide of the formula (IX):

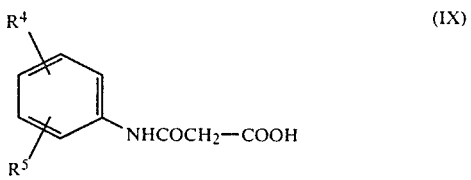

wherein $R^4$ and $R^5$ are as above defined at a temperature of from 100° C. to 200° C. for two to twenty-four hours in a suitable dehydrating ring closure reagent such as, for example, polyphosphoric acid, concentrated sulfuric acid or the like.

There are also many other routes to synthesize the compound of the formula (V). They are, for example, as follows. Malonic acid bianilide is heated at 250° to 350° C. in vacuo; anthranilic acid ester is made to react with diketene; anthranilic acid is heated in acetic anhydride; 3-carboxymethylbenzoisoxazole is used as a starting material; 2-methyl-3,1-benzoxazin-4-one is made to react with sodium alkoxide in xylene, and the like.

Further, 4-hydroxy-2-quinolone derivatives of the present invention can also be synthesized in a single step by heating benzoylmalonic acid ester with aniline in nitrobenzene.

4-Hydroxy-2-quinolone derivatives prepared by the above methods can easily be isolated and purified by conventional methods such as, for example, recrystallization, chromatography and the like. Thus, prepared present invention compounds can be made into salts thereof with conventional pharmaceutically acceptable basic compounds. Examples of said basic compounds are sodium hydroxide, potassium hydroxide, aluminum hydroxide, calcium hydroxide, sodium carbonate, potassium carbonate, sodium bicarbonate, potassium bicarbonate and other inorganic basic compounds as well as morpholine, piperidine, triethylamine and other organic basic substances. Basic amino acids are, of course, included in the basic compounds.

Compounds according to the present invention exhibit anti-allergic action and, accordingly, can be administered to patients suffering from asthma, hay fever, hives and atopic dermatitis. Further, they exhibit anti-inflammatory action and, consequently, they can be administered to patients suffering from chronic rheumatoid arthritis, pain after operations, ankylosing spondylitis, osteoarthritis of large joints (such as hips, knees and shoulders), acute gouty arthritis, acute inflammation of upper respiratory, toothache and menstrual pains.

Pharmaceutically acceptable salts of the compounds of the formula (I) are prepared in a conventional manner.

Representative compounds of the present invention include:

3-Benzoyl-6-chloro-4-hydroxy-2-quinolone, 3-benzoyl-7-chloro-4-hydroxy-2-quinolone, 3-benzoyl-8-chloro-4-hydroxy-6-methyl-2-quinolone, 3-benzoyl-6,8-dichloro-4-hydroxy-2-quinolone, 3-benzoyl-7-ethoxy-8-nitro-4-hydroxy-2-quinolone, 3-benzoyl-6,7-dimethoxy-4-hydroxy-2-quinolone, 3-benzoyl-4-hydroxy-7-nitro-2-quinolone, 3-benzoy-6-cyano-4-hydroxy-2-quinolone, methyl 3-benzoyl-4-hydroxy-2-quinolone-5-carboxylate, methyl 3-benzoyl-4-hydroxy-2-quinolone-6-carboxylate, methyl 3-benzoyl-4-hydroxy-2-quinolone-7-carboxylate, methyl 3-benzoyl-4-hydroxy-2-quinolone-7-carboxylate, 3-benzoyl-4-hydroxy-2-quinolone-5-carboxylic acid, 3-benzoyl-4-hydroxy-2-quinolone-6-carboxylic acid, 3-benzoyl-4-hydroxy-2-quinolone-7-carboxylic acid, 3-benzoyl-4-hydroxy-2-quinolone-8-carboxylic acid, 3-benzoyl-4-hydroxy-6-methyl-2-quinolone, 3-benzoyl-4-hydroxy-7-methyl-2-quinolone, 3-benzoyl-4-hydroxy-8-methyl-2-quinolone, 3,-benzoyl-6,7-dimethyl-4-hydroxy-2-quinolone, 3-benzoyl-6,8-dimethyl-4-hydroxy-2-quinolone, 3-benzoyl-6-isopropyl-4-hydroxy-2-quinolone, 3-benzoy-6-n-butyl-4-hydroxy-2-quinolone, 3-benzoyl-6-n-hexyl-4-hydroxy-2-quinolone, 4-hydroxy-3-(2-methoxybenzoyl)-2-quinolone, 3-(2-ethoxybenzoyl)-4-hydroxy-2-quinolone, 4-hydroxy-3-(2-isopropoxybenzoyl)-2-quinolone, 4-hydroxy-3-(4-methoxybenzoyl)-2-quinolone, 3-(2,4-dimethoxybenzoyl)-4-hydroxy-2-quinolone, 3-(3,4-dimethoxybenzoyl)-4-hydroxy-2-quinolone, 3-(3,4-dimethoxybenzoyl)-4-hydroxy-6-methyl-2-quinolone, 3-(3,4-dimethoxybenzoyl)-4-hydroxy-7-nitro-2-quinolone, 3-(3,4-dimethoxybenzoyl)-4-hydroxy-8-methyl-2-quinolone, 4-hydroxy-3-(2-isopropoxy-5-methoxybenzoyl)-2-quinolone, 4-hydroxy-3-(2,3,4-trimethoxybenzoyl)-2-quinolone, 4-hydroxy-3-(3,4,5-trimethoxybenzoyl)-2-quinolone, 4-hydroxy-3-(2,4,5-trimethoxybenzoyl)-2-quinolone, 3-(2-chlorobenzoyl)-4-hydroxy-2-quinolone, 3-(2-chlorobenzoyl)-4-hydroxy-6-isopropyl-2-quinolone, 3-(2-chlorobenzoyl)-6,8-dimethyl-4-hydroxy-2-quinolone, 3-(3-chlorobenzoyl)-4-hydroxy-2-quinolone, 3-(4-chlorobenzoyl)-4-hydroxy-2-quinolone, 3-(2-bromo-4-cyanobenzoyl)-4-hydroxy-2-quinolone, 3-(3,4-dichlorobenzoyl)-4-hydroxy-2-quinolone, 3-(2,5-dichloro-4-methylbenzoyl)-4-hydroxy-2-quinolone, 4-hydroxy-3-(2-methylbenzoyl)-2-quinolone, 4-hydroxy-3-(4-methylbenzoyl)-2-quinolone, 3-(2,4-dimethylbenzoyl)-4-hydroxy-2-quinolone, 4-hydroxy-3-(3-trifluoromethylbenzoyl)-2-quinolone, 4-hydroxy-3-(4-isopropylbenzoyl)-2-quinolone, 4-hydroxy-3-(4-n-pentylbenzoyl)-2-quinolone, 4-hydroxy-3-(4-nitrobenzoyl)-2-quinolone, 4-hydroxy-6-isopropyl-3-(4-nitrobenzoyl)-2-quinolone, 6,8-dimethyl-4-hydroxy-3-(4-nitrobenzoyl)-2-quinolone, 4-hydroxy-3-(4-methoxycarbonylbenzoyl)-2-quinolone, 3-(4-carboxybenzoyl)-4-hydroxy-2-quinolone, 4-hydroxy-6-methyl-3-(2,3,4-trimethoxybenzoyl)-2-quinolone, 4-hydroxy-8-methyl-3-(2,3,4-trimethoxybenzoyl)-2-quinolone, 4-hydroxy-7-nitro-3-(2,3,4-trimethoxybenzoyl)-2-quinolone, and the like.

The compounds of the present invention and their pharmaceutically acceptable salts may be formulated into pharmaceutical compositions using techniques per se known. Pharmaceutical compositions may thus be prepared which are useful for administration to humans and animals suffering from asthma, hay fever, hives, atopic dermatitis, inflammations such as that resulting from chronic rheumatoid arthritis, post-operational pain, arthrosis deformans, low back pain, ankylosing spondylitis, osteoarthritis of large joints, acute upper respiratory inflammation, toothache and dysmenorrhea. Such pharmaceutical compositions are produced by combining a therapeutically effective amount of a compound of the formula (I) or a pharmaceutically acceptable salt thereof with a pharmaceutically acceptable carrier.

The present invention also includes methods of effecting anti-inflammatory, anti-allergenic, expectorant and antitussive action in humans and animals which comprises administering a therapeutically effective amount of a compound of the formula (I) or a pharmaceutically acceptable salt thereof in combination with a pharmaceutically acceptable carrier.

Suitable pharmaceutical compositions according to the present invention may contain from 0.1% to 99% of a compound of the formula (I) or a pharmaceutically acceptable salt thereof or more preferably from about 0.5% to about 90%. Such pharmaceutical compositions are preferably in dosage unit form; i.e., physically discrete units containing a predetermined amount of the compound of the formula (I) or a pharmaceutically acceptable salt thereof corresponding to a fraction or multiple of the dose which is calculated to produce the desired therapeutic response. The dosage units can contain one, two, three, four or more single doses or, alternatively, one half, third or fourth of a single dose. A single dose preferably contains an amount sufficient to produce the desired therapeutic effect upon administration at one application of one or more dosage units according to a predetermined dosage regimen, usually a whole, half, third or quarter of the daily dosage administered once, twice, three or four times a day.

Although the dosage and dosage regimen must in each case be carefully adjusted, utilizing sound professional judgment and considering the age, weight and condition of the recipient, the route of administration and the nature and gravity of the illness, generally the dosage will be as follows: for oral administration from about 1 to about 1000 mg one to three times per day of said compound or salt thereof for an average adult. For parenteral administration and as eye drops, from about 0.1 to about 50 mg three to four times per day. For rectal administration, from about 1 to about 500 mg one to three times per day. For inhalation and nasal administration, from about 0.1 to about 100 mg two to three times per day. For topical application such as ointment, from about 1 to about 100 mg two to three times per day. In some instances, a sufficient therapeutic effect can be obtained at a lower dose, while in others a larger dose will be required.

Oral administration can be effected utilizing solid and liquid dosage unit forms such as powders, tablets, dragees, capsules, granulates, suspensions, solutions and the like.

Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and, optionally, with a binder such as carboxymethyl cellulose, an alginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acacia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds and pharmaceutically acceptable salts of the present invention can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous solution, while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccarin, and the like can also be added.

Where appropriate, dosage unit formulations for oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsifiers can also be added.

Rectal administration can be effected to utilizing suppositories in which the compound is admixed with low-melting, water-soluble or insoluble solids such as polyethylene glycol, cocoa butter, higher esters as for example myristyl palmitate, or mixtures thereof.

The compositions and methods of the present invention are particularly useful for oral administration.

The compounds of the present invention have been evaluated for their anti-allergenic action by passive cutaneous anaphylatic assay (PCA) in rats and by measuring the anti-SRS-A action using ileus of guinea pigs.

TEST METHOD NO. 1 (PCA)

(i) Antiserum abundant in homocytotropic antibody is prepared by the same method as Tada and Okumura did (cf. Journal of Immunology, vol. 106, page 1002, 1976). Thus, 1 mg (calculated as an amount of protein) of DNP-As (2,4-dinitrophenyl-coupled ascaris extract) prepared by methods of Strejan and Campbell (Journal of Immunology, vol. 98, p. 893, 1971) and of Eisen (Journal of Amer. Chem. Soc., vol. 85, p 4593, 1953) and $1 \times 10^{10}$ pertussis vaccine are administered to each paw of Wister strain rats (180 to 200 grams body weights) by dividing the dose by four. Five days later, 0.5 mg of DNP-As is administered into muscle of back. Eight days later from the initial immunization, blood is taken from descending aorta under anesthetizing with ether, the resulting serum is stored at $-80°$ and is melted before use.

(ii) Effect of tested compounds is investigated as follows:

Anti-serum obtained by the method (i) is diluted with physiological saline solution double by double successively and 0.05 ml of each diluted solution is administered into back of Wister strain rats (140 to 160 grams body weight) subcutaneously. After 72 hours, a solution of 2 mg (calculated as protein) of DNP-As and 2.5 mg of Evans Blue dissolved in 1 ml of physiological saline solution is administered intraveously at a dose of 5 ml/kg. After 30 minutes from antigen solution administration, the animals are killed and diameters of blue spots appeared at the place where antiserum is administered are measured. The PCA test is conducted by the same method as already described using a diluted solutions of antiserum which always show 10 mm or more of spot diameters and the effect of the test compounds is judged. Thus antiserum diluted solutions are administered to two places in back. Test compounds are administered orally at the dose of 10 mg/kg one hour before administration of antigen solution. From the skin of reacted parts of killed animals, leaked or emitted dyestuff is extracted and the amount of the dyestuff is measured. The inhibition ratio is calculated by the following expression:

Inhibition Ratio = $(1 - A'/A) \times 100$ in which $A'$ is an amount of dyestuff in the group treated with the test compounds and $A$ is that in the control group.

TEST METHOD NO. 2

Anti-SRS-As action (An anti-action against slow reacting substance of anaphylaxis).

Hartley strain male guinea pigs (300 to 350 grams body weight) are killed and 1.0 to 1.5 cm of ileus is immeidiately excised from ileocecal parts and is suspended in 10 ml of Tyrode solution (95% $O_2$-5% $CO_2$ saturation) containing $10^{-7}$ g/ml of atropine and $10^{-6}$ g/ml of pyrilamine. SRS-A (20 units) (the amount of SRS-A showing the same shrinkage as 5 ng of histamine is defined as 1 unit) prepared by using sensitized guinea pig lung is given to cause shrinkage there. Then antagonistic action of test compounds treated five minutes ago against the shrinkage is measured and recorded via isotonic transducer.

Inhibition Ratio of Test Compd
(%) = $(1 - A'/A) \times 100$ in which $A'$ is a height of shrinkage of SRS-A + test compound and $A$ is that of SRS-A.

TABLE 1

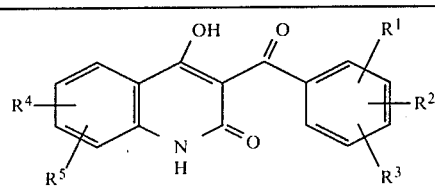

| Example No. | $R^1, R^2, R^3$ | $R^4, R^5$ | PCA Inhibition Ratio % | $10^{-6}$ M SRS-A Inhibition Ratio % |
|---|---|---|---|---|
| 8 | H | 7-Cl | 16.5 | 26.2 |
| 10 | H | 7-$NO_2$ | 33.4 | 22.3 |
| 3 | H | 5-COOMe | 26.9 | 26.4 |
| 13 | H | 8-COOMe | 25.7 | 19.8 |
| 16 | H | 8-COOH | 30.9 | 22.4 |
| 17 | H | 6-Me | 35.4 | 21.9 |
| 18 | H | 7-Me | 26.0 | 21.3 |
| 19 | H | 8-Me | 29.6 | 19.0 |
| 20 | H | 6,7-(Me)$_2$ | 17.4 | 23.5 |
| 22 | H | 6-n-$C_4H_9$ | 17.4 | 39.5 |
| 23 | H | 6-n-$C_6H_{13}$ | 13.1 | 83.3 (32.8) |
| 24 | 2'-OMe | H | 24.7 | 20.2 |
| 28 | 2',4'-(OMe)$_2$ | H | 21.2 | 42.9 |
| 2 | 3',4'-(OMe)$_2$ | H | 25.5 | 24.2 |
| 29 | 3',4'-(OMe)$_2$ | 6-Me | 12.1 | 42.1 |
| 30 | 3',4'-(OMe)$_2$ | 7-$NO_2$ | 18.7 | 26.7 |
| 31 | 3',4'-(OMe)$_2$ | 8-Me | 20.4 | 20.5 |
| 32 | 2',3',4'-(OMe)$_3$ | H | 16.3 | 100 (83.3) |
| 35 | 2'-Cl | H | 45.6 | 32.6 |

TABLE 1-continued

| Example No. | $R^1, R^2, R^3$ | $R^4, R^5$ | PCA Inhibition Ratio % | $10^{-6}$ M SRS-A Inhibition Ratio % |
|---|---|---|---|---|
| 36 | 2'-Cl | 6-i-$C_3H_7$ | 12.4 | 60.0 |
| 37 | 2'-Cl | 6,8-(Me)$_2$ | 20.8 | 28.3 |
| 39 | 4'-Cl | H | 19.8 | 27.0 |
| 46 | 4'-n-$C_5H_{11}$ | H | 3.2 | 26.9 |
| 47 | 4'-$NO_2$ | H | 49.4 | 22.0 |
| 48 | 4'-$NO_2$ | 6-i-$C_3H_7$ | 8.6 | 29.8 |
| 51 | 4'-COOMe | H | 7.4 | 50.0 |
| 7 (Sodium Salt) | H | 6-n-hexyl | 15.2 | 91.2 |
| 55 (Calcium Salt) | H | 6-n-hexyl | 13.6 | 85.6 |

The value in ( ) is for $10^{-7}$ M

The anti-inflammatory action of the compounds of the present invention were evaluated by measuring the inhibition against carrageein edema as set forth below.

Carrageenin edema at hind foot of rats:

EXPERIMENTAL METHOD

SD-strain rats of body weights of around 150 grams were used, each group consisting of five rats. A solution (0.1 ml) of 0.5% carrageenin dissolved in physiological saline water was hypodermically injected into right hind foot pat of the rats and, one hour prior to the injection of carrageenin, 200 mg/kg of test compound was given per os. Foot volumes of the rats before the carrageenin treatment and those of three hours after the treatment were measured and the differences were compared with those of the control group to determine the effect of the compounds.

Results of the representative compounds are as follows:

| Example Number | % Inhibition |
|---|---|
| 1 | 42.1 |
| 18.1 | 22.0 |
| 19 | 70.0 |
| 3 | 32.8 |
| 43 | 15.7 |
| 44 | 15.9 |
| 5 | 32.1 |
| 30 | 21.3 |
| 48 | 12.5 |
| 31 | 77.5 |
| 23 | 15.9 |
| 54 | 13.1 |
| 59 | 12.8 |
| 55 | 10.0 |
| Control: Acetylsalicylic Acid | 31.6 |

Acute toxicity was determined two weeks after oral administration of 400 mg/kg to male mice. Four mice (denominator) are used in each group and the dead numbers are given as the numerator. The compounds of the present invention show little, if any, toxicity. Representative data are given below.

| Example Number | Lethal Ratio |
| --- | --- |
| 10 | 0/4 |
| 13 | 1/4 |
| 16 | 0/4 |
| 19 | 0/4 |
| 23 | 0/4 |
| 32 | 0/4 |
| 35 | 0/4 |
| 47 | 0/4 |

Lethal ratios for all other compounds are 0/4 at doses of 200 mg/kg. It is therefore apparent that they are all safe compounds.

The following non-limitative examples more particularly illustrate the compounds of the present invention and the formulation of various pharmaceutical preparations.

Examples of pharmaceutical preparations:

(1) Capsules mainly composed of 4-hydroxy-3-(2,3,4-trimethoxybenzoyl)-2-quinolone (Example No. 32 compound).

The compound of Example 32 is mixed uniformly with diluents as per the following ratios and filled in hard gelatin capsules to give the desired preparation.

| | |
| --- | --- |
| Compounds of Example 32 | 50 mg |
| Hydroxypropyl cellulose of lower degree of substitution | 20 mg |
| Lactose | 84 mg |
| Starch | 40 mg |
| Talc | 5 mg |
| Magnesium stearate | 1 mg |
| Mixed to make | 200 mg per capsule |

(2) Tablets containing 3-(2-chlorobenzoyl)-4-hydroxy-2-quinoline (compound of Example 35) as a main constituent.

Pulverized compound of Example 35 (100 mg) is mixed with 100 mg of lactose, 75 mg of crystalline cellulose and 40 mg of potato starch, kneaded with a binder solution prepared from 10 mg of polyvinyl alcohol, the mixture is passed through a sieve of 16 mesh, the resulting granules are dried, and once again passed through a sieve of 16 mesh. Then the granules are mixed with 3 mg of magnesium stearate and 7 mg of talc and compressed into tablets. The resulting tablets are, if necessary, coated with conventional coating base or with sucrose.

EXAMPLE 1

3-Benzoyl-6-chloro-4-hydroxy-2-quinolone

To 6.0 grams of ethyl 2-amino-5-chlorobenzoate is added 6.4 grams of ethyl benzoylacetate, the mixture is heated at 180° to 190° C. for ten hours, cooled, crystals separated out therefrom are collected by filtration, and washed with methanol to give 5.1 grams of ethyl 2-benzoylacetylamino-5-chlorobenzoate, colorless needles. To 200 ml of ethanol is added 640 mg of metal sodium, then 4.8 grams of ethyl 2-benzoylacetylamino-5-chlorobenzoate is added thereto, the mixture is heated to reflux for two hours, cooled, poured into ice water, adjusted to pH 3 with 10% hydrochloric acid, crystals separated out therefrom are collected by filtration, and recystallized from dimethylformamide and methanol to give 1.9 grams of 3-benzoyl-6-chloro-4-hydroxy-2-quinoline, pale yellow needles, melting at above 300° C.

Elementary analysis calculated for $C_{16}H_{10}ClNO_3$: C 63.12, H 3.36, N 4.67; Found: C 64.38, H 3,14, N 4.59.

EXAMPLE 2

3-(3,4-Dimethoxybenzoyl)-4-hydroxy-2-quinolone

Ethyl anthranilate (1.44 grams) and 2.2 grams of ethyl 3,4-dimethoxybenzoylacetate are dissolved in 100 ml of xylene and heated to reflux for five hours with 200 mg of sodium ethoxide. After cooling, crystals are separated out and collected by filtration and recrystallized from methanol to give 0.5 grams of 3-(3,4-dimethoxybenzoyl)-4-hydroxy-2-quinolone, pale yellow needles, melting point 235° to 236° C.

Elementary analysis calculated for $C_{18}H_{15}NO_5$: C 66.45, H 4.65, N 4.31; Found: C 66.17, H 4.69, N 4.07.

EXAMPLE 3

Methyl 3-benzoyl-4-hydroxy-2-quinolone-5-carboxylate

A mixture of 2.1 grams of dimethyl 3-aminophthalate, 1.4 grams of benzoylacetic acid and 2.9 grams of dicyclohexlcarbodiimide is dissolved in 15 ml of tetrahydrofuran and the mixture is stirred at room temperature for eighteen hours. The insoluble matter are removed by filtration, the filtrate is concentrated, and 1.9 grams of dimethyl 3-benzoylacetylaminophthalate, colorless crystals, melting point 100° to 103° C. is obtained. This (1.9 grams) is dissolved in 30 ml of methanol, heated to reflux for four hours with 0.48 grams of sodium hydride, cooled, adjusted to pH 3 with diluted hydrochloric acid, crystals separated out therefrom are collected by filtration and recrystallized from methanol to give 1.3 grams of methyl 3-benzoyl-4-hydroxy-2-quinolone-5-carboxylate, pale yellow needles, melting point 263° to 265° C.

Elementary analysis calculated for $C_{18}H_{13}NO_5$: C 66.87, H 4.05, N 4.33; Found: C 66.99, H 3.80, N 4.03.

EXAMPLE 4

3-Benzoyl-4-hydroxy-2-quinolone-5-carboxylic acid

To 0.6 grams of methyl 3-benzoyl-4-hydroxy-2-quinolone-5-carboxylate are added 1.5 grams of sodium hydroxide, 30 ml of water and 30 ml of dimethyl sulfoxide, the mixture is heated at 100° to 120° C. for three hours with stirring, cooled, acidified and diluted hydrochloric acid, and crystals separated out therefrom are collected by filtration to give 0.54 grams of 3-benzoyl-4-hydroxy-2-quinolone-5-carboxylic acid, colorless powder, melting at above 300° C.

Elementary analysis calculated for $C_{17}H_{11}NO_5$: C 66.02, H 3.59, N 4.53; Found: C 65.78, H 3.47, N 4.41.

EXAMPLE 5

3-Benzoyl-4-hydroxy-6-isopropyl-2-quinoline (a) p-Isopropylaniline (13.5 grams) and 100 grams of diethyl malonate are heated at 175° to 180° C. for two hours, an excess of diethyl malonate is removed in vacuo, to the residue are added 8 grams of potassium hydroxide and 300 ml of methanol, and the mixture is heated to reflux for three hours. After evaporation of methanol, the residue is dissolved in water, the solution is acidified with diluted hydrochloric acid, and crystals separated out therefrom are collected by filtration. The resulting crystals (16.3 grams) are heated in 100 grams of polyphosphoric acid at 160° C. for four hours, poured into ice water, crystals separated out therefrom are collected by filtration, and washed with water to give 11 grams of 4-hydroxy-6-isopropyl-2-quinoline, pale brown crystals, melting at above 300° C.

To 10 ml of nitrobenzene is added 3.3 grams of anhydrous aluminum chloride, benzoyl chloride is dropped thereinto with stirring, to the resulting uniform solution is added 2.5 grams of 4-hydroxy-6-isopropyl-2-quinolone, the mixture is heated with stirring at 100° C. for eight hours, then concentrated hydrochloric acid is added to make the reaction solution decomposed, water is added thereto, crystals separated out therefrom are collected by filtration, washed with ether and methanol, and recrystallized from chloroform and methanol to give 1.6 grams of 3-benzoyl-4-hydroxy-6-isopropyl-2-quinolone, pale yellow needles, melting point 270° C.

Elementary analysis calculated for $C_{19}H_{17}NO_3$: C 74.25, H 5.58, N 4.56; Found: C 74.38, H 5.51, N 4.61.

(b) To 2.5 grams of 4-hydroxy-6-isopropyl-2-quinolone was added 50 ml of dimethyl formamide, then 600 mg of 50% sodium hydride was added with stirring, the mixture was stirred for 30 minutes, and 1.73 grams of benzoic chloride was dropped therein. The mixture was stirred at room temperature for one hour, poured over into ice water, and extracted with chloroform. The solvent was evaporated from the extract, 10 ml of nitrobenzene was added to the residue, and the mixture was heated on a steam bath for 4 hours. To this was added concentrated hydrochloric acid to decompose the reaction solution, then water was added thereto, and crystals separated out therefrom were collected by filtration. The crystals were washed with ether and methanol and recrystallized from methanol and chloroform to give 1 gram of 3-benzoyl-4-hydroxy-6-isopropyl-2-quinolonem pale yellow needles, m.p. 270° C.

EXAMPLE 6

3-Benzoyl-6,8-dichloro-4-hydroxy-2-quinolone

Ethyl 2-amino-3,5-dichlorobenzoate (4.0 grams) is dissolved in 100 ml of chloroform, 2.5 ml of pyridine is added, the mixture is heated to reflux for twenty-four hours with 2.5 ml of acetyl chloride, the solvent is evaporated therefrom, n-hexane is added thereto, and colorless crystals are obtained. The resulting crystals (3.5 grams) is heated to reflux for five hours with 100 ml of toluene and 610 mg of sodium hydride, cooled, 100 mg of water is added thereto, an aqueous layer is separated therefrom, acidified with diluted hydrochloric acid, and crystals separated out therefrom are collected by filtration to give 1.5 grams of 6,8-dichloro-4-hydroxy-2-quinoline, pale yellow powder, melting at above 300° C.

Benzoyl chloride (0.93 gram) is added to a mixture of 1.5 grams of anhydrous aluminum chloride and 10 ml of nitrobenzene, the mixture is stirred at room temperature until it becomes uniform, stirred at 105° to 110° C. for eight hours with 1.26 grams of 6,8-dichloro-4-hydroxy-2-quinolone, decomposed with concentrated hydrochloric acid, small amount of water is added thereto, and crystals separated out therefrom are collected by filtration. The crystals are washed with water and then washed with methanol and ether to give 1.2 grams of 3-benzoyl-6,8-dichloro-4-hydroxy-2-quinolone, pale yellow powder, melting point 258° to 259° C.

Elementary analysis calculated for $C_{16}H_9Cl_2NO_3$: C 57.51, H 2.71, N 4.19; Found: C 57.31, H 2.64, N 4.11.

EXAMPLE 7

3-Benzoyl-6-n-hexyl-4-hydroxy-2-quinolone sodium salt

Sodium hydroxide (560 mg) is dissolved in 100 ml of methanol, the mixture is heated with stirring with 5.5 grams of 6-n-hexyl-4-hydroxy-2-quinolone, cooled, insoluble matters are removed by filtration, the filtrate is concentrated and evaporated to dryness, and the residue is recrystallized from iso-propyl alcohol to give 5 grams of sodium salt of 3-benzoyl-6-n-hexyl-4-hydroxy-2-quinolone, yellow crystals, melting point 217° to 221° C.

Elementary analysis calculated for $C_{22}H_{22}NO_3Na$: C 71.15, H 5.97, N 3.77; Found C 70.87, H 5.99, N 3.68.

The compounds of Examples 8–63 set forth in the table below are produced by procedures analogous to those of the foregoing examples.

| Example No. | $R^1$, $R^2$, $R^3$ | $R^4$, $R^5$ | Appearance | M.p. (°C.) | Experimental formula | Elementary Analysis (%) (Upper Column: Calc'd Lower Column: Found) |
|---|---|---|---|---|---|---|
| 8 | H | 7-Cl | Colorless needles | >300 | $C_{15}H_{10}ClNO_3$ | C 64.12 H 3.36 N 4.67<br>C 64.34 H 3.08 N 4.51 |
| 9 | H | 6.7-(OMe)$_2$ | Pale yellow powder | >300 | $C_{18}H_{15}NO_5$ | C 66.45 H 4.65 N 4.31<br>C 66.66 H 4.45 N 4.26 |
| 10 | H | 7-NO$_2$ | Yellow needles | >300 | $C_{10}H_{10}N_2O_5$ | C 61.94 H 3.25 N 9.03<br>C 61.91 H 2.96 N 8.84 |
| 11 | H | 6-COOMe | Colorless powder | 279~281 | $C_{18}H_{13}NO_5$ | C 66.87 H 4.05 N 4.33<br>C 66.65 H 3.76 N 4.13 |
| 12 | H | 7-COOMe | Pale yellow powder | 285~287 | $C_{18}H_{13}NO_5$ | C 66.87 H 4.05 N 4.33<br>C 66.88 H 3.83 N 4.43 |
| 13 | H | 8-COOMe | Pale yellow powder | 184~186 | $C_{18}H_{13}NO_5$ | C 66.87 H 4.05 N 4.33<br>C 66.72 H 4.02 N 4.20 |
| 14 | H | 6-COOH | Colorless powder | >300 | $C_{17}H_{11}NO_5$ | C 66.02 H 3.59 N 4.53<br>C 66.09 H 3.33 N 4.48 |
| 15 | H | 7-COOH | Colorless powder | >300 | $C_{17}H_{11}NO_5$ | C 66.02 H 3.59 N 4.53<br>C 65.95 H 3.35 N 4.57 |
| 16 | H | 8-COOH | Pale yellow powder | 286~288 | $C_{17}H_{11}NO_5$ | C 66.02 H 3.59 N 4.53<br>C 65.73 H 3.58 N 4.45 |
| 17 | H | 6-Me | Yellow needles | 295~296 | $C_{17}H_{13}NO_3$ | C 73.11 H 4.68 N 5.02<br>C 73.37 H 4.53 N 4.97 |
| 18 | H | 7-Me | Yellow needles | >300 | $C_{17}H_{13}NO_3$ | C 73.11 H 4.68 N 5.02<br>C 73.35 H 4.52 N 4.93 |

-continued

| Example No. | R¹, R², R³ | R⁴, R⁵ | Appearance | M.p. (°C.) | Experimental formula | Elementary Analysis (%) (Upper Column: Calc'd Lower Column: Found) |
|---|---|---|---|---|---|---|
| 19 | H | 8-Me | Pale yellow needles | 273~274 | $C_{17}H_{13}NO_3$ | C 73.11 H 4.68 N 5.02<br>C 73.09 H 4.49 N 5.19 |
| 20 | H | 6,7-(Me)₂ | Pale yellow powder | 292 | $C_{18}H_{15}NO_3$ | C 73.70 H 5.15 N 4.78<br>C 73.58 H 4.97 N 4.49 |
| 21 | H | 6,8-(Me)₂ | Pale yellow needles | >300 | $C_{18}H_{15}NO_3$ | C 73.70 H 5.15 N 4.78<br>C 73.41 H 4.99 N 4.66 |
| 22 | H | 6-n-C₄H₉ | Pale yellow needles | 230~231 | $C_{20}H_{19}NO_3$ | C 74.74 H 5.96 N 4.36<br>C 74.91 H 6.04 N 4.35 |
| 23 | H | 6-n-C₆H₁₃ | Pale yellow needles | 206~207 | $C_{22}H_{23}NO_3$ | C 75.62 H 6.63 N 4.01<br>C 75.72 H 6.59 N 4.04 |
| 24 | 2'-OMe | H | Yellow powder | 275~276 | $C_{17}H_{13}NO_4$ | C 69.14 H 4.44 N 4.74<br>C 69.40 H 4.14 N 4.65 |
| 25 | 2'OEt | H | Colorless powder | 265~267 | $C_{18}H_{15}N_4$ | C 69.89 H 4.89 N 4.53<br>C 70.08 H 4.82 N 4.66 |
| 26 | 2'O—i-C₃H₇ | H | Colorless powder | 260~262 | $C_{19}H_{17}NO_4$ | C 70.57 H 5.30 N 4.33<br>C 70.52 H 5.36 N 4.26 |
| 27 | 4'-OMe | H | Pale yellow powder | 275~280 | $C_{17}H_{13}NO_4$ | C 69.14 H 4.44 N 4.74<br>C 68.84 H 4.02 N 4.46 |
| 28 | 2',4'-(OMe)₂ | H | Pale yellow powder | 260~262 | $C_{18}H_{15}NO_5$ | C 66.45 H 4.65 N 4.31<br>C 66.60 H 4.59 N 4.15 |
| 29 | 3',4'-(OMe)₂ | 6-Me | Pale yellow powder | 282~284 | $C_{19}H_{17}NO_5$ | C 67.25 H 5.05 N 4.13<br>C 67.43 H 4.92 N 4.13 |
| 30 | 3',4'-(OMe)₂ | 7-NO₂ | Yellow powder | 285~290 | $C_{18}H_{14}N_2O_7$ | C 58.38 H 3.81 N 7.57<br>C 58.09 H 4.18 N 7.33 |
| 31 | 3',4'-(OMe)₂ | 8-Me | Colorless powder | 259~261 | $C_{19}H_{17}NO_5$ | C 67.25 H 5.05 N 4.13<br>C 67.49 H 4.95 N 3.96 |
| 32 | 2',3',4'-(OMe)₃ | H | Pale yellow crystals | 247~249 | $C_{19}H_{17}NO_6$ | C 64.22 H 4.82 N 3.94<br>C 64.50 H 4.64 N 4.10 |
| 33 | 3',4',5'-(OMe)₃ | H | Colorless needles | 199~200 | $C_{19}H_{17}NO_5$ | C 64.22 H 4.82 N 3.94<br>C 64.26 H 4.90 N 3.79 |
| 34 | 2',4',5'-(OMe)₃ | H | Yellow needles | 228~230 | $C_{19}H_{17}NO_6$ | C 64.22 H 4.82 N 3.94<br>C 64.47 H 4.71 N 3.81 |
| 35 | 2'-Cl | H | Colorless powder | >300 | $C_{16}H_{10}ClNO_3$ | C 64.12 H 3.34 N 4.68<br>C 64.40 H 3.18 N 4.54 |
| 36 | 2'-Cl | 6-i-C₃H₇ | Pale yellow needles | 224~225 | $C_{19}H_{15}ClNO_3$ | C 66.77 H 4.72 N 4.10<br>C 66.97 H 4.61 N 4.14 |
| 37 | 2'-Cl | 6,8-(Me)₂ | Pale yellow needles | >300 | $C_{18}H_{14}ClNO_3$ | C 65.96 H 4.31 N 4.27<br>C 66.18 H 4.23 N 4.09 |
| 38 | 3'-Cl | H | Pale yellow needles | 268 | $C_{16}H_{10}ClNO_3$ | C 64.12 H 3.36 N 4.67<br>C 64.33 H 3.18 N 4.53 |
| 39 | 4'-Cl | H | Colorless powder | >300 | $C_{15}H_{10}ClNO_3$ | C 64.12 H 3.36 N 4.67<br>C 64.06 H 3.12 N 4.69 |
| 40 | 3',4'-(Cl)₂ | H | Yellow powder | 285~290 | $C_{15}H_9Cl_2NO_3$ | C 57.51 H 2.71 N 4.19<br>C 57.61 H 2.41 N 3.91 |
| 41 | 2'-Me | H | Colorless powder | 292~295 | $C_{17}H_{13}NO_3$ | C 73.11 H 4.69 N 5.02<br>C 72.92 H 4.44 N 5.00 |
| 42 | 4'-Me | H | Pale yellow needles | 290~292 | $C_{17}H_{13}NO_3$ | C 73.11 H 4.69 N 5.02<br>C 73.19 H 4.43 N 5.02 |
| 43 | 2',4'-(Me)₂ | H | Colorless powder | 253~255 | $C_{18}H_{15}NO_3$ | C 73.70 H 5.15 N 4.78<br>C 73.87 H 5.08 N 4.71 |
| 44 | 3'-CF₃ | H | Colorless powder | 258~260 | $C_{17}H_{10}F_3NO_3$ | C 61.27 H 3.02 N 4.20<br>C 61.55 H 2.87 N 4.05 |
| 45 | 4'-i-C₃H₇ | H | Colorless powder | 286~288 | $C_{19}H_{17}NO_3$ | C 74.25 H 5.58 N 4.56<br>C 74.45 H 5.33 N 4.27 |
| 46 | 4'-n-C₅H₁₁ | H | Pale brown powder | 199~202 | $C_{20}H_{21}NO_3$ | C 74.28 H 6.55 N 4.33<br>C 74.28 H 6.35 N 4.38 |
| 47 | 4'-NO₂ | H | Pale yellow needles | >300 | $C_{16}H_{10}N_2O_5$ | C 61.94 H 3.25 N 9.03<br>C 61.64 H 2.99 N 8.95 |
| 48 | 4'-NO₂ | 6-i-C₃H₇ | Yellow powder | >300 | $C_{19}H_{16}N_2O_5$ | C 64.77 H 4.58 N 7.95<br>C 64.67 H 4.40 N 7.80 |
| 49 | 4'-NO₂ | 6,8-(Me)₂ | Yellow powder | >300 | $C_{18}H_{14}NO_5$ | C 63.90 H 4.17 N 8.28<br>C 63.93 H 4.11 N 8.21 |
| 50 | 4'-COOMe | H | Colorless | >300 | $C_{18}H_{13}NO_5$ | C 66.87 H 4.05 N 4.33 |

-continued

| Example No. | $R^1, R^2, R^3$ | $R^4, R^5$ | Appearance | M.p. (°C.) | Experimental formula | Elementary Analysis (%) (Upper Column: Calc'd Lower Column: Found) |
|---|---|---|---|---|---|---|
| 51 | 4'-COOH | H | powder Colorless powder | >300 | $C_{17}H_{11}NO_5$ | C 66.99 H 3.86 N 4.18 C 66.02 H 3.59 N 4.53 C 65.77 H 3.38 N 4.25 |
| 52 | 2',3',4'-(OMe)$_3$ | 6-Me | Pale yellow crystals | 231~233 | $C_{20}H_{19}NO_6$ | C 65.03 H 5.19 N 3.79 C 65.04 H 5.20 N 3.68 |
| 53 | 2',3',4'-(OMe)$_3$ | 8-Me | Pale yellow crystals | 244~246 | $C_{20}H_{19}NO_6$ | C 65.03 H 5.19 N 3.79 C 65.21 H 5.13 N 3.63 |
| 54 | 2',3',4'-(OMe)$_3$ | 7-NO$_2$ | Pale yellow crystals | >300 | $C_{19}H_{16}N_2O_8$ | C 57.00 H 4.03 N 7.00 C 56.83 H 4.04 N 6.84 |
| 55 (calcium salt) | H | 6-n-hexyl | White powder | >300 | $C_{44}H_{44}N_2O_6Ca \cdot H_2O$ | C 70.00 H 6.14 N 3.71 C 70.18 H 6.00 N 3.46 |
| 56 | 2,4-Cl | 6-n-hexyl | yellow needles | 294–297° | (hereinafter, results of elementary analysis are omitted.) | |
| 57 | 4-n-pentyl | 6-n-hexyl | yellow flakes | 180–182° | | |
| 58 | 4-Et | 6-n-hexyl | pale yellow needles | 231–233° | | |
| 59 | 4-OMe | 6-n-hexyl | yellow needles | 203–206° | | |
| 60 | H | 6-n-pentyl | yellow needles | 218–219.5° | | |
| 61 | H | 6-n-octyl | yellow needles | 207–208.5° | | |
| 62 | 4-NO$_2$ | 6-n-hexyl | yellow needles | 264–265° | | |
| 63 | 2-Cl | 6-n-hexyl | yellow needles | 184–185° | | |

What is claimed is:

1. A compound of the formula (I):

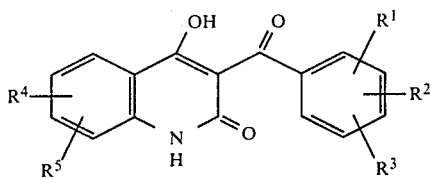

or a pharmaceutically acceptable salt thereof wherein $R^1$, $R^2$ and $R^3$ are each hydrogen, alkyl of 1 to 8 carbon atoms, alkoxy of 1 to 5 carbon atoms, halo, nitro, cyano, halo lower alkyl of 1 to 3 carbon atoms or COOR$^6$ wherein R$^6$ is hydrogen or alkyl of 1 to 3 carbon atoms, and $R^4$ and $R^5$ are each hydrogen, alkyl of 1 to 8 carbon atoms, halo, nitro, cyano, halo lower alkyl of 1 to 3 carbon atoms or COOR$^6$ wherein R$^6$ is as above defined, provided that all of $R^1$, $R^2$, $R^3$, $R^4$ and $R^5$ are not simultaneously hydrogen.

2. A compound according to claim 1 wherein $R^1$, $R^2$ and $R^3$ are each hydrogen, methyl, ethyl, propyl, isopropyl, butyl, isobutyl, tert butyl, pentyl, hexyl, heptyl, octyl, methoxy, ethoxy, propoxy, isopropoxy, butoxy, tert butoxy, fluoro, chloro, bromo, iodo, nitro, cyano or trifluoromethyl and $R^4$ and $R^5$ are each hydrogen, methyl, ethyl, propyl, isopropyl, butyl, isobutyl, tertbutyl, pentyl, hexyl, heptyl, octyl, fluoro, chloro, bromo, iodo, nitro, cyano or trifluoromethyl.

3. A compound according to claim 1 wherein $R^1$, $R^2$ and $R^3$ are each hydrogen, methyl, ethyl, propyl, isopropyl, butyl, isobutyl, tert butyl, methoxy, ethoxy, propoxy, isopropoxy, fluoro, chloro, bromo, nitro, cyano, trifluoromethyl or COOR$^6$ wherein R$^6$ is hydrogen, methyl, ethyl or propyl and $R^4$ and $R^5$ are each hydrogen, methyl, ethyl, propyl, isopropyl, butyl, isobutyl, tert-butyl, fluoro, chloro, bromo, nitro, cyano, trifluoromethyl or COOR$^6$ wherein R$^6$ is as above defined.

4. A compound according to claim 1 in the form of a pharmaceutically acceptable salt.

5. A pharmaceutical composition useful for effecting anti-inflammatory, anti-allergenic, antitussive or expectorant action in humans and animals which comprises a therapeutically effective amount of a compound of the formula (I):

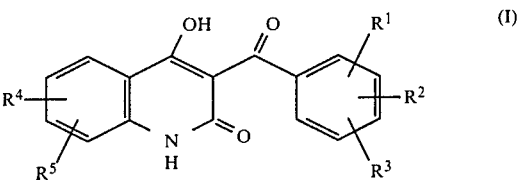

or a pharmaceutically acceptable salt thereof wherein $R^1$, $R^2$ and $R^3$ are each hydrogen, alkyl of 1 to 8 carbon atoms, alkoxy of 1 to 5 carbon atoms, halo, nitro, cyano, halo lower alkyl of 1 to 3 carbon atoms or COOR$^6$ wherein R$^6$ is hydrogen or alkyl of 1 to 3 carbon atoms, and $R^4$ and $R^5$ are each hydrogen, alkyl of 1 to 8 carbon atoms, halo, nitro, cyano, halo lower alkyl of 1 to 3 carbon atoms or COOR$^6$ wherein R$^6$ is as above defined, provided that all of $R^1$, $R^2$, $R^3$, $R^4$ and $R^5$ are not simultaneously hydrogen, in combination with a pharmaceutically acceptable carrier.

6. A composition according to claim 5 wherein $R^1$, $R^2$ and $R^3$ are each hydrogen, methyl, ethyl, propyl, isopropyl, butyl, isobutyl, tert butyl, pentyl, hexyl, heptyl, octyl, methoxy, ethoxy, propoxy, isopropoxy, butoxy, tert butoxy, fluoro, chloro, bromo, iodo, nitro, cyano or trifluoromethyl and $R^4$ and $R^5$ are each hydrogen, methyl, ethyl, propyl, isopropyl, butyl, isobutyl, tert-butyl, pentyl, hexyl, heptyl, octyl, fluoro, chloro, bromo, iodo, nitro, cyano or trifluoromethyl.

7. A composition according to claim 5 wherein $R^1$, $R^2$ and $R^3$ are each hydrogen, methyl, ethyl, propyl, isopropyl, butyl, isobutyl, tert butyl, methoxy, ethoxy, propoxy, isopropoxy, fluoro, chloro, bromo, nitro, cyano, trifluoromethyl or COOR$^6$ wherein R$^6$ is hydrogen, methyl, ethyl or propyl and $R^4$ and $R^5$ are each hydrogen, methyl, ethyl, propyl, isopropyl, butyl, isobutyl, tert-butyl, fluoro, chloro, bromo, nitro, cyano, trifluoromethyl or COOR⁶ wherein R⁶ is as above defined.

8. A composition according to claim 5 wherein the compound is in the form of a pharmaceutically acceptable salt.

9. A method of effecting anti-inflammatory, anti-allergenic, antitussive and expectorant action in humans and animals which comprises administering to a human or animal in need thereof a therapeutically effective amount of a compound of the formula (I):

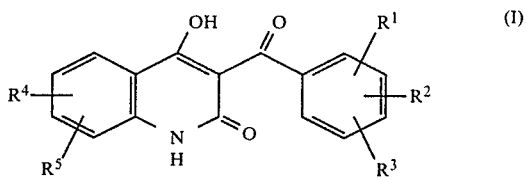

or a pharmaceutically acceptable salt thereof wherein $R^1$, $R^2$ and $R^3$ are each hydrogen, alkyl of 1 to 8 carbon atoms, alkoxy of 1 to 5 carbon atoms, halo, nitro, cyano, halo lower alkyl of 1 to 3 carbon atoms or COOR⁶ wherein R⁶ is hydrogen or alkyl of 1 to 3 carbon atoms, and $R^4$ and $R^5$ are each hydrogen, alkyl of 1 to 8 carbon atoms, halo, nitro, cyano, halo lower alkyl of 1 to 3 carbon atoms or COOR⁶ wherein R⁶ is as above defined, provided that all of $R^1$, $R^2$, $R^3$, $R^4$ and $R^5$ are not simultaneously hydrogen, in combination with a pharmaceutically acceptable carrier.

10. A method according to claim 9 wherein $R^1$, $R^2$ and $R^3$ are each hydrogen, methyl, ethyl, propyl, isopropyl, butyl, isobutyl, tert butyl, pentyl, hexyl, heptyl, octyl, methoxy, ethoxy, propoxy, isopropoxy, butoxy, tert butoxy, fluoro, chloro, bromo, iodo, nitro, cyano or trifluoromethyl and $R^4$ and $R^5$ are each hydrogen, methyl, ethyl, propyl, isopropyl, butyl, isobutyl, tert-butyl, pentyl, hexyl, heptyl, octyl, fluoro, chloro, bromo, iodo, nitro, cyano or trifluoromethyl.

11. A method according to claim 9 wherein $R^1$, $R^2$ and $R^3$ are each hydrogen, methyl, ethyl, propyl, isopropyl, butyl, isobutyl, tert butyl, methoxy, ethoxy, propoxy, isopropoxy, fluoro, chloro, bromo, nitro, cyano, trifluoromethyl or COOR⁶ wherein R⁶ is hydrogen, methyl, ethyl or propyl and $R^4$ and $R^5$ are each hydrogen, methyl, ethyl, propyl, isopropyl, butyl, isobutyl, tert-butyl, fluoro, chloro, bromo, nitro, cyano, trifluoromethyl or COOR⁶ wherein R⁶ is as above defined.

12. A method according to claim 9 wherein the compound is in the form of a pharmaceutically acceptable salt.

13. The compound according to claim 1 which is:
3-benzoyl-6-chloro-4-hydroxy-2-quinolone,
3-benzoyl-7-chloro-4-hydroxy-2-quinolone,
3-benzoyl-8-chloro-4-hydroxy-6-methyl-2-quinolone,
3-benzoyl-6,8-dichloro-4-hydroxy-2-quinolone,
3-benzoyl-4-hydroxy-7-nitro-2-quinolone,
3-benzoyl-6-cyano-4-hydroxy-2-quinolone,
methyl 3-benzoyl-4-hydroxy-2-quinolone-5-carboxylate,
methyl 3-benzoyl-4-hydroxy-2-quinolone-6-carboxylate,
methyl 3-benzoyl-4-hydroxy-2-quinolone-7-carboxylate,
3-benzoyl-4-hydroxy-2-quinolone-5-carboxylic acid,
3-benzoyl-4-hydroxy-2-quinolone-6-carboxylic acid,
3-benzoyl-4-hydroxy-2-quinolone-7-carboxylic acid,
3-benzoyl-4-hydroxy-2-quinolone-8-carboxylic acid,
3-benzoyl-4-hydroxy-6-methyl-2-quinolone,
3-benzoyl-4-hydroxy-7-methyl-2-quinolone,
3-benzoyl-4-hydroxy-8-methyl-2-quinolone,
3-benzoyl-6,7-dimethyl-4-hydroxy-2-quinolone,
3-benzoyl-6,8-dimethyl-4-hydroxy-2-quinolone,
3-benzoyl-6-isopropyl-4-hydroxy-2-quinolone,
3-benzoyl-6-n-butyl-4-hydroxy-2-quinolone,
3-benzoyl-6-n-hexyl-4-hydroxy-2-quinolone,
4-hydroxy-3-(2-methoxybenzoyl)-2-quinolone,
3-(2-ethoxybenzoyl)-4-hydroxy-2-quinolone,
4-hydroxy-3-(2-isopropoxybenzoyl)-2-quinolone,
4-hydroxy-3-(4-methoxybenzoyl)-2-quinolone,
3-(2,4-dimethoxybenzoyl)-4-hydroxy-2-quinolone,
3-(3,4-dimethoxybenzoyl)-4-hydroxy-2-quinolone,
3-(3,4-dimethoxybenzoyl)-4-hydroxy-6-methyl-2-quinolone,
3-(3,4-dimethoxybenzoyl)-4-hydroxy-7-nitro-2-quinolone,
3-(3,4-dimethoxybenzoyl)-4-hydroxy-8-methyl-2-quinolone,
4-hydroxy-3-(2-isopropoxy-5-methoxybenzoyl)-2-quinolone,
4-hydroxy-3-(2,3,4-trimethoxybenzoyl)-2-quinolone,
4-hydroxy-3-(3,4,5-trimethoxybenzoyl)-2-quinolone,
4-hydroxy-3-(2,4,5-trimethoxybenzoyl)-2-quinolone,
3-(2-chlorobenzoyl)-4-hydroxy-2-quinolone,
3-(2-chlorobenzoyl)-4-hydroxy-6-isopropyl-2-quinolone,
3-(2-chlorobenzoyl)-6,8-dimethyl-4-hydroxy-2-quinolone,
3-(3-chlorobenzoyl)-4-hydroxy-2-quinolone,
3-(4-chlorobenzoyl)-4-hydroxy-2-quinolone,
3-(2-bromo-4-cyanobenzoyl)-4-hydroxy-2-quinolone,
3-(3,4-dichlorobenzoyl)-4-hydroxy-2-quinolone,
3-(2,5-dichloro-4-methylbenzoyl)-4-hydroxy-2-quinolone,
4-hydroxy-3-(2-methylbenzoyl)-2-quinolone,
4-hydroxy-3-(4-methylbenzoyl)-2-quinolone,
3-(2,4-dimethylbenzoyl)-4-hydroxy-2-quinolone,
4-hydroxy-3-(3-trifluoromethylbenzoyl)-2-quinolone,
4-hydroxy-3-(4-isopropylbenzoyl)-2-quinolone,
4-hydroxy-3-(4-n-pentylbenzoyl)-2-quinolone,
4-hydroxy-3-(4-nitrobenzoyl)-2-quinolone,
4-hydroxy-6-isopropyl-3-(4-nitrobenzoyl)-2-quinolone,
6,8-dimethyl-4-hydroxy-3-(4-nitrobenzoyl)-2-quinolone,
4-hydroxy-3-(4-methoxycarbonylbenzoyl)-2-quinolone,
3-(4-carboxybenzoyl)-4-hydroxy-2-quinolone,
4-hydroxy-6-methyl-3-(2,3,4-trimethoxybenzoyl-2-quinolone,
4-hydroxy-8-methyl-3-(2,3,4-trimethoxybenzoyl-2-quinolone, or
4-hydroxy-7-nitro-3-(2,3,4-trimethoxybenzoyl-2-quinolone.

14. A composition according to claim 5 wherein the compound is:
3-benzoyl-6-chloro-4-hydroxy-2-quinolone,
3-benzoyl-7-chloro-4-hydroxy-2-quinolone,
3-benzoyl-8-chloro-4-hydroxy-6-methyl-2-quinolone,
3-benzoyl-6,8-dichloro-4-hydroxy-2-quinolone,
3-benzoyl-4-hydroxy-7-nitro-2-quinolone,
3-benzoyl-6-cyano-4-hydroxy-2-quinolone,
methyl 3-benzoyl-4-hydroxy-2-quinolone-5-carboxylate,
methyl 3-benzoyl-4-hydroxy-2-quinolone-6-carboxylate, methyl 3-benzoyl-4-hydroxy-2-quinolone-7-carboxylate,
3-benzoyl-4-hydroxy-2-quinolone-5-carboxylic acid,
3-benzoyl-4-hydroxy-2-quinolone-6-carboxylic acid,
3-benzoyl-4-hydroxy-2-quinolone-7-carboxylic acid,
3-benzoyl-4-hydroxy-2-quinolone-8-carboxylic acid,
3-benzoyl-4-hydroxy-6-methyl-2-quinolone,
3-benzoyl-4-hydroxy-7-methyl-2-quinolone,
3-benzoyl-4-hydroxy-8-methyl-2-quinolone,
3-benzoyl-6,7-dimethyl-4-hydroxy-2-quinolone,
3-benzoyl-6,8-dimethyl-4-hydroxy-2-quinolone,
3-benzoyl-6-isopropyl-4-hydroxy-2-quinolone,
3-benzoyl-6-n-butyl-4-hydroxy-2-quinolone,
3-benzoyl-6-n-hexyl-4-hydroxy-2-quinolone,
4-hydroxy-3-(2-methoxybenzoyl)-2-quinolone,
3-(2-ethoxybenzoyl)-4-hydroxy-2-quinolone,
4-hydroxy-3-(2-isopropoxybenzoyl)-2-quinolone,
4-hydroxy-3-(4-methoxybenzoyl)-2-quinolone,
3-(2,4-dimethoxybenzoyl)-4-hydroxy-2-quinolone,
3-(3,4-dimethoxybenzoyl)-4-hydroxy-2-quinolone,
3-(3,4-dimethoxybenzoyl)-4-hydroxy-6-methyl-2-quinolone,
3-(3,4-dimethoxybenzoyl)-4-hydroxy-7-nitro-2-quinolone,
3-(3,4-dimethoxybenzoyl)-4-hydroxy-8-methyl-2-quinolone,
4-hydroxy-3-(2-isopropoxy-5-methoxybenzoyl)-2-quinolone,
4-hydroxy-3-(2,3,4-trimethoxybenzoyl)-2-quinolone,
4-hydroxy-3-(3,4,5-trimethoxybenzoyl)-2-quinolone,
4-hydroxy-3-(2,4,5-trimethoxybenzoyl)-2-quinolone,
3-(2-chlorobenzoyl)-4-hydroxy-2-quinolone,
3-(2-chlorobenzoyl)-4-hydroxy-6-isopropyl-2-quinolone,
3-(2-chlorobenzoyl)-6,8-dimethyl-4-hydroxy-2-quinolone,
3-(3-chlorobenzoyl)-4-hydroxy-2-quinolone,
3-(4-chlorobenzoyl)-4-hydroxy-2-quinolone,
3-(2-bromo-4-cyanobenzoyl)-4-hydroxy-2-quinolone,
3-(3,4-dichlorobenzoyl)-4-hydroxy-2-quinolone,
3-(2,5-dichloro-4-methylbenzoyl)-4-hydroxy-2-quinolone,
4-hydroxy-3-(2-methylbenzoyl)-2-quinolone,
4-hydroxy-3-(4-methylbenzoyl)-2-quinolone,
3-(2,4-dimethylbenzoyl)-4-hydroxy-2-quinolone,
4-hydroxy-3-(3-trifluoromethylbenzoyl)-2-quinolone,
4-hydroxy-3-(4-isopropylbenzoyl)-2-quinolone,
4-hydroxy-3-(4-n-pentylbenzoyl)-2-quinolone,
4-hydroxy-3-(4-nitrobenzoyl)-2-quinolone,
4-hydroxy-6-isopropyl-3-(4-nitrobenzoyl)-2-quinolone,
6,8-dimethyl-4-hydroxy-3-(4-nitrobenzoyl)-2-quinolone,
4-hydroxy-3-(4-methoxycarbonylbenzoyl)-2-quinolone,
3-(4-carboxybenzoyl)-4-hydroxy-2-quinolone,
4-hydroxy-6-methyl-3-(2,3,4-trimethoxybenzoyl-2-quinolone,
4-hydroxy-8-methyl-3-(2,3,4-trimethoxybenzoyl-2-quinolone, or
4-hydroxy-7-nitro-3-(2,3,4-trimethoxybenzoyl-2-quinolone.

15. A method according to claim 9 wherein the compound is:
3-benzoyl-6-chloro-4-hydroxy-2-quinolone,
3-benzoyl-7-chloro-4-hydroxy-2-quinolone,
3-benzoyl-8-chloro-4-hydroxy-6-methyl-2-quinolone,
3-benzoyl-6,8-dichloro-4-hydroxy-2-quinolone,
3-benzoyl-4-hydroxy-7-nitro-2-quinolone,
3-benzoyl-6-cyano-4-hydroxy-2-quinolone,
methyl 3-benzoyl-4-hydroxy-2-quinolone-5-carboxylate,
methyl 3-benzoyl-4-hydroxy-2-quinolone-6-carboxylate,
methyl 3-benzoyl-4-hydroxy-2-quinolone-7-carboxylate,
3-benzoyl-4-hydroxy-2-quinolone-5-carboxylic acid,
3-benzoyl-4-hydroxy-2-quinolone-6-carboxylic acid,
3-benzoyl-4-hydroxy-2-quinolone-7-carboxylic acid,
3-benzoyl-4-hydroxy-2-quinolone-8-carboxylic acid,
3-benzoyl-4-hydroxy-6-methyl-2-quinolone,
3-benzoyl-4-hydroxy-7-methyl-2-quinolone,
3-benzoyl-4-hydroxy-8-methyl-2-quinolone,
3-benzoyl-6,7-dimethyl-4-hydroxy-2-quinolone,
3-benzoyl-6,8-dimethyl-4-hydroxy-2-quinolone,
3-benzoyl-6-isopropyl-4-hydroxy-2-quinolone,
3-benzoyl-6-n-butyl-4-hydroxy-2-quinolone,
3-benzoyl-6-n-hexyl-4-hydroxy-2-quinolone,
4-hydroxy-3-(2-methoxybenzoyl)-2-quinolone,
3-(2-ethoxybenzoyl)-4-hydroxy-2-quinolone,
4-hydroxy-3-(2-isopropoxybenzoyl)-2-quinolone,
4-hydroxy-3-(4-methoxybenzoyl)-2-quinolone,
3-(2,4-dimethoxybenzoyl)-4-hydroxy-2-quinolone,
3-(3,4-dimethoxybenzoyl)-4-hydroxy-2-quinolone,
3-(3,4-dimethoxybenzoyl)-4-hydroxy-6-methyl-2-quinolone,
3-(3,4-dimethoxybenzoyl)-4-hydroxy-7-nitro-2-quinolone,
3-(3,4-dimethoxybenzoyl)-4-hydroxy-8-methyl-2-quinolone,
4-hydroxy-3-(2-isopropoxy-5-methoxybenzoyl)-2-quinolone,
4-hydroxy-3-(2,3,4-trimethoxybenzoyl)-2-quinolone,
4-hydroxy-3-(3,4,5-trimethoxybenzoyl)-2-quinolone,
4-hydroxy-3-(2,4,5-trimethoxybenzoyl)-2-quinolone,
3-(2-chlorobenzoyl)-4-hydroxy-2-quinolone,
3-(2-chlorobenzoyl)-4-hydroxy-6-isopropyl-2-quinolone,
3-(2-chlorobenzoyl)-6,8-dimethyl-4-hydroxy-2-quinolone,
3-(3-chlorobenzoyl)-4-hydroxy-2-quinolone,
3-(4-chlorobenzoyl)-4-hydroxy-2-quinolone,
3-(2-bromo-4-cyanobenzoyl)-4-hydroxy-2-quinolone,
3-(3,4-dichlorobenzoyl)-4-hydroxy-2-quinolone,
3-(2,5-dichloro-4-methylbenzoyl)-4-hydroxy-2-quinolone,
4-hydroxy-3-(2-methylbenzoyl)-2-quinolone,
4-hydroxy-3-(4-methylbenzoyl)-2-quinolone,
3-(2,4-dimethylbenzoyl)-4-hydroxy-2-quinolone,
4-hydroxy-3-(3-trifluoromethylbenzoyl)-2-quinolone,
4-hydroxy-3-(4-isopropylbenzoyl)-2-quinolone,
4-hydroxy-3-(4-n-pentylbenzoyl)-2-quinolone,
4-hydroxy-3-(4-nitrobenzoyl)-2-quinolone,
4-hydroxy-6-isopropyl-3-(4-nitrobenzoyl)-2-quinolone,
6,8-dimethyl-4-hydroxy-3-(4-nitrobenzoyl)-2-quinolone,
4-hydroxy-3-(4-methoxycarbonylbenzoyl)-2-quinolone,
3-(4-carboxybenzoyl)-4-hydroxy-2-quinolone,
4-hydroxy-6-methyl-3-(2,3,4-trimethoxybenzoyl-2-quinolone,
4-hydroxy-8-methyl-3-(2,3,4-trimethoxybenzoyl-2-quinolone, or
4-hydroxy-7-nitro-3-(2,3,4-trimethoxybenzoyl-2-quinolone.

* * * * *